United States Patent
Junio

(10) Patent No.: US 12,193,768 B2
(45) Date of Patent: Jan. 14, 2025

(54) SYSTEM AND METHOD FOR ALIGNING AN IMAGING DEVICE

(71) Applicant: MAZOR ROBOTICS LTD., Caesarea (IL)

(72) Inventor: Dany Junio, Tel Aviv-Jaffa (IL)

(73) Assignee: MAZOR ROBOTICS LTD., Caesarea (IL)

(*) Notice: Subject to any disclaimer, the term of this patent is extended or adjusted under 35 U.S.C. 154(b) by 969 days.

(21) Appl. No.: 16/853,990

(22) Filed: Apr. 21, 2020

(65) Prior Publication Data

US 2021/0322112 A1 Oct. 21, 2021

(51) Int. Cl.
*A61B 34/30* (2016.01)
*A61B 34/00* (2016.01)
*G06T 7/00* (2017.01)
*G06T 7/73* (2017.01)
(Continued)

(52) U.S. Cl.
CPC .............. *A61B 34/30* (2016.02); *A61B 34/25* (2016.02); *G06T 7/0014* (2013.01); *G06T 7/73* (2017.01); *A61B 2034/2065* (2016.02); *A61B 2034/2074* (2016.02); *A61B 2090/376* (2016.02); *G06T 2207/10121* (2013.01); *G06T 2207/20084* (2013.01)

(58) Field of Classification Search
CPC . A61B 34/30; A61B 34/25; A61B 2034/2065; A61B 2034/2074; A61B 2090/376; A61B 2017/00725; A61B 2034/2051; A61B 2034/2055; G06T 2207/10121; G06T 2207/20084; G06T 7/0014; G06T 7/73
See application file for complete search history.

(56) References Cited

U.S. PATENT DOCUMENTS

| 7,142,633 B2 | 11/2006 | Eberhard et al. |
| 7,231,073 B2 | 6/2007 | Tamaka |
| 7,366,562 B2 | 4/2008 | Dukesherer et al. |

(Continued)

FOREIGN PATENT DOCUMENTS

| CN | 110599508 | 12/2019 |
| DE | 102008050572 | 4/2010 |

(Continued)

OTHER PUBLICATIONS

Han et al. "A targeting method for robot-assisted percutaneous needle placement under fluoroscopy guidance," Computer Assisted Surgery, 2019, vol. 24, No. S1, pp. 44-52.

(Continued)

*Primary Examiner* — Baisakhi Roy
(74) *Attorney, Agent, or Firm* — Sheridan Ross P.C.

(57) ABSTRACT

A method of aligning an imaging device in connection with robotic surgery includes causing a robot to position a reference target over a body of a patient; receiving image data from an imaging device; identifying, with an image processing algorithm, at least a first portion of an anatomical element in the image data; identifying, with a target detection algorithm, at least a first portion of a reference target in the image data; comparing a determined location of the imaging device, the reference target, and the anatomical element to yield a location determination and causing at least one of the robot to re-position the reference target or the imaging device to re-position.

20 Claims, 6 Drawing Sheets

(51) Int. Cl.
*A61B 34/20* (2016.01)
*A61B 90/00* (2016.01)

(56) References Cited

U.S. PATENT DOCUMENTS

| | | | |
|---|---|---|---|
| 8,103,079 B2 | 1/2012 | Saito | |
| 9,289,268 B2 * | 3/2016 | Ramraj | A61B 8/0833 |
| 9,463,073 B2 | 10/2016 | Gill et al. | |
| 9,491,415 B2 | 11/2016 | Deurz et al. | |
| 9,968,502 B2 | 5/2018 | Hight et al. | |
| 10,058,338 B2 | 8/2018 | Shoham | |
| 10,426,554 B2 | 10/2019 | Siewerdsen et al. | |
| 10,478,143 B2 | 11/2019 | Merlet et al. | |
| 10,551,821 B2 | 2/2020 | Yamaguchi et al. | |
| 11,331,153 B2 * | 5/2022 | Crawford | A61B 90/37 |
| 2003/0135115 A1 * | 7/2003 | Burdette | A61N 5/103 |
| | | | 600/437 |
| 2006/0025677 A1 | 2/2006 | Verard et al. | |
| 2008/0214922 A1 | 9/2008 | Hartmann et al. | |
| 2009/0278702 A1 | 11/2009 | Graumann et al. | |
| 2009/0287223 A1 * | 11/2009 | Pua | A61B 90/11 |
| | | | 600/443 |
| 2014/0163736 A1 | 6/2014 | Alizian et al. | |
| 2015/0055086 A1 * | 2/2015 | Fonte | G06F 16/22 |
| | | | 700/98 |
| 2015/0335390 A1 | 11/2015 | Gill | |
| 2016/0253797 A1 | 9/2016 | Lang et al. | |
| 2016/0310761 A1 * | 10/2016 | Li | A61N 5/1039 |
| 2016/0324585 A1 * | 11/2016 | Noonan | A61B 90/37 |
| 2017/0348061 A1 * | 12/2017 | Joshi | A61B 90/90 |
| 2018/0000415 A1 * | 1/2018 | Gupta | A61B 5/684 |
| 2018/0021102 A1 | 1/2018 | Azizian et al. | |
| 2018/0318012 A1 | 11/2018 | Arno et al. | |
| 2019/0110855 A1 | 4/2019 | Harral et al. | |
| 2020/0100855 A1 * | 4/2020 | Leparmentier | A61B 34/30 |
| 2020/0214656 A1 | 7/2020 | Shirota et al. | |
| 2020/0312028 A1 * | 10/2020 | Charvat | G05D 1/101 |
| 2021/0068907 A1 * | 3/2021 | Fuerst | A61B 90/361 |
| 2021/0093396 A1 * | 4/2021 | Chappuis | A61B 34/76 |
| 2021/0186615 A1 * | 6/2021 | Shmayahu | A61B 90/03 |
| 2021/0228281 A1 | 7/2021 | Calloway | |
| 2022/0241037 A1 * | 8/2022 | Crawford | A61M 5/172 |

FOREIGN PATENT DOCUMENTS

| | | |
|---|---|---|
| EP | 3578128 | 12/2019 |
| WO | WO 2010/064234 | 6/2010 |
| WO | WO 2019/012520 | 1/2019 |
| WO | WO 2019/169178 | 9/2019 |

OTHER PUBLICATIONS

International Search Report and Written Opinion for International (PCT) Patent Application No. PCT/US2021/026429, dated Jul. 26, 2021, 8 pages.
Official Action for U.S. Appl. No. 16/854,011, dated Feb. 25, 2022 8 pages.
U.S. Appl. No. 16/854,011, filed Apr. 21, 2020, Junio.
Notice of Allowance for U.S. Appl. No. 16/854,011, dated Jun. 8, 2022 7 pages.
Extended Search Report for European Patent Application No. 21792352.3, dated Apr. 19, 2024, 10 pages.

* cited by examiner

SYSTEM AND METHOD FOR ALIGNING AN IMAGING DEVICE

FIELD

The present technology is related generally to imaging devices and, more particularly, to aligning an imaging device for robotic surgery.

BACKGROUND

Robots are increasingly be used to assist with or to perform surgical procedures. Before a robot can participate in a surgical procedure, however, a robotic coordinate system must be mapped to a patient coordinate system or vice versa, so that the robot's movements relative to the patient enable the robot to operate on the correct portion(s) of the patient. As part of this mapping or registration, an imaging device may be used to obtain one or more images of a reference target held by the robot and of the anatomical element of the patient on which a surgical procedure will be performed. Such images may only be useful, however, if the anatomical element and the reference target are fully captured in the frame of the imaging device, which may require a trial and error process to ensure proper alignment of the imaging device and the reference target with the anatomical element.

Conventional methods for alignment of a patient and a surgical robot rely on comparing at least one preoperative image of a patient's anatomy (used, for example, for planning a surgery to be conducted on the imaged anatomy) with two intraoperative orthogonal images of the same anatomy and of an aspect of a surgical robot taken during the initial setup of the operation. By aligning identical features in the images with each other, and determining the position of the robot based on the aspect of the surgical robot in the intraoperative images, the preoperative planning space can be registered to the intraoperative patient space and robotic space, such that the surgery can proceed as planned. Such conventional methods of registration are time consuming and complex, and every image taken exposes the patient to additional, potentially harmful, radiation.

SUMMARY

Embodiments of the present disclosure advantageously provide simplified approaches to aligning an imaging device and a robot for robotic surgery. Embodiments of the present disclosure beneficially decrease overall operating time by reducing the initial setup time needed to align the imaging device and/or robot with the patient and thus to register robotic space with patient space. Embodiments of the present disclosure may also beneficially reduce radiation exposure to the patient by reducing the number of images needed to achieve such registration.

A system for aligning an imaging device and a reference target for robotic surgery according to one embodiment of the present disclosure comprises: a processor; and a memory storing instructions for execution by the processor that, when executed, cause the processor to: transmit first instructions configured to cause a robot to position a reference target proximate a body of a patient, receive image data from an imaging device, determine, using an image processing algorithm, whether all, some, or none of an anatomical element is represented in the image data, to yield a first determination, determine, using a target detection algorithm, whether all, some, or none of the reference target is represented in the image data, to yield a second determination, generate, based on the first determination and the second determination, a repositioning requirement and transmit second instructions for repositioning at least one of the imaging device and the reference target based on the repositioning requirement.

The image processing algorithm may use a neural network. The imaging device may be a fluoroscopy device. The memory further may include instructions that, when executed, cause the processor to: receive second image data, determine, using the target detection algorithm, that only a portion or none of the reference target is represented in the second image data to yield a third determination, generate, based on the third determination, a second repositioning requirement, and transmit third instructions for repositioning the reference target based on the second repositioning requirement. The third instructions may be configured to reposition the reference target toward a center of an image represented by the second image data. The memory may further includes instructions that, when executed, cause the processor to: receive second image data, determine, using the image processing algorithm, that only a portion or none of the anatomical element is represented in the second image data to yield a third determination, generate, based on the third determination, a second repositioning requirement, and transmit third instructions for repositioning the imaging device based on the second repositioning requirement. The third instructions for repositioning the imaging device may further comprise instructions for repositioning the imaging device in a direction of the portion of the anatomical element not represented in the second image data. The third instructions may be configured to cause automatic repositioning of the imaging device. The memory may further include instructions that, when executed, cause the processor to: receive second image data, determine, using the image processing algorithm and the target detection algorithm, that only a portion or none of both the reference target and the anatomical element is represented in the image data to yield a third determination, generate, based on the third determination, a second repositioning requirement, and transmit third instructions for repositioning the reference target and the imaging device based on the second repositioning requirement.

A method of aligning an imaging device and a reference target for robotic surgery according to one embodiment of the present disclosure comprises: causing a robot to position a reference target proximate a body of a patient; receiving image data from an imaging device; determining, using an image processing algorithm, whether all, some, or none of an anatomical element is represented in the image data, to yield a first determination; determining, using a target detection algorithm, whether all, some, or none of the reference target is represented in the image data, to yield a second determination; generating, based on the first determination and the second determination, a repositioning requirement; and transmitting second instructions for repositioning at least one of the imaging device and the reference target based on the repositioning requirement.

The method may further comprise: receiving second image data from the imaging device; determining, using the target detection algorithm, that the entire reference target is represented in the second image data; and determining, using the image processing algorithm, that the entire anatomical element is represented in the second image data. The method may further comprise: receiving second image data; determining, using the target detection algorithm, that only a portion or none of the reference target is represented in the second image data to yield a third determination; generating, based on the third determination, a second repositioning requirement; and transmitting third instructions for repositioning the reference target based on the second repositioning requirement. The third instructions for repositioning the reference target may further comprise repositioning the reference target toward a center of an image represented by the second image data.

The method may further comprise receiving second image data from the imaging device; determining, using the image processing algorithm, that only a portion or none of the anatomical element is represented in the second image data to yield a third determination; generating, based on the third determination, a second repositioning requirement; and transmitting third instructions for repositioning the imaging device based on the second repositioning requirement. The third instructions for repositioning the imaging device may further comprise repositioning the imaging device in a direction of the portion of the anatomical element not represented in the second image data. The third instructions may be configured to automatically cause repositioning of the imaging device.

Another system for aligning an imaging device and a reference target for surgery according to one embodiment may comprise: at least one communication interface for communicating with an imaging device and; a robot supporting a reference target with a robotic arm; a processor; and a memory storing instructions for execution by the processor that, when executed, cause the processor to: receive image data, via the communication interface, from the imaging device, determine, using an image processing algorithm, whether all, some, or none of an anatomical element is represented in the image data, to yield a first determination, determine, using a target detection algorithm, whether all, some, or none of the reference target is represented in the image data, to yield a second determination, generate, based on the first determination and the second determination, a repositioning requirement, and transmit second instructions for repositioning at least one of the imaging device and the reference target based on the repositioning requirement.

The imaging device may be a fluoroscopy device. The anatomical element may correspond to a vertebral anatomy.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
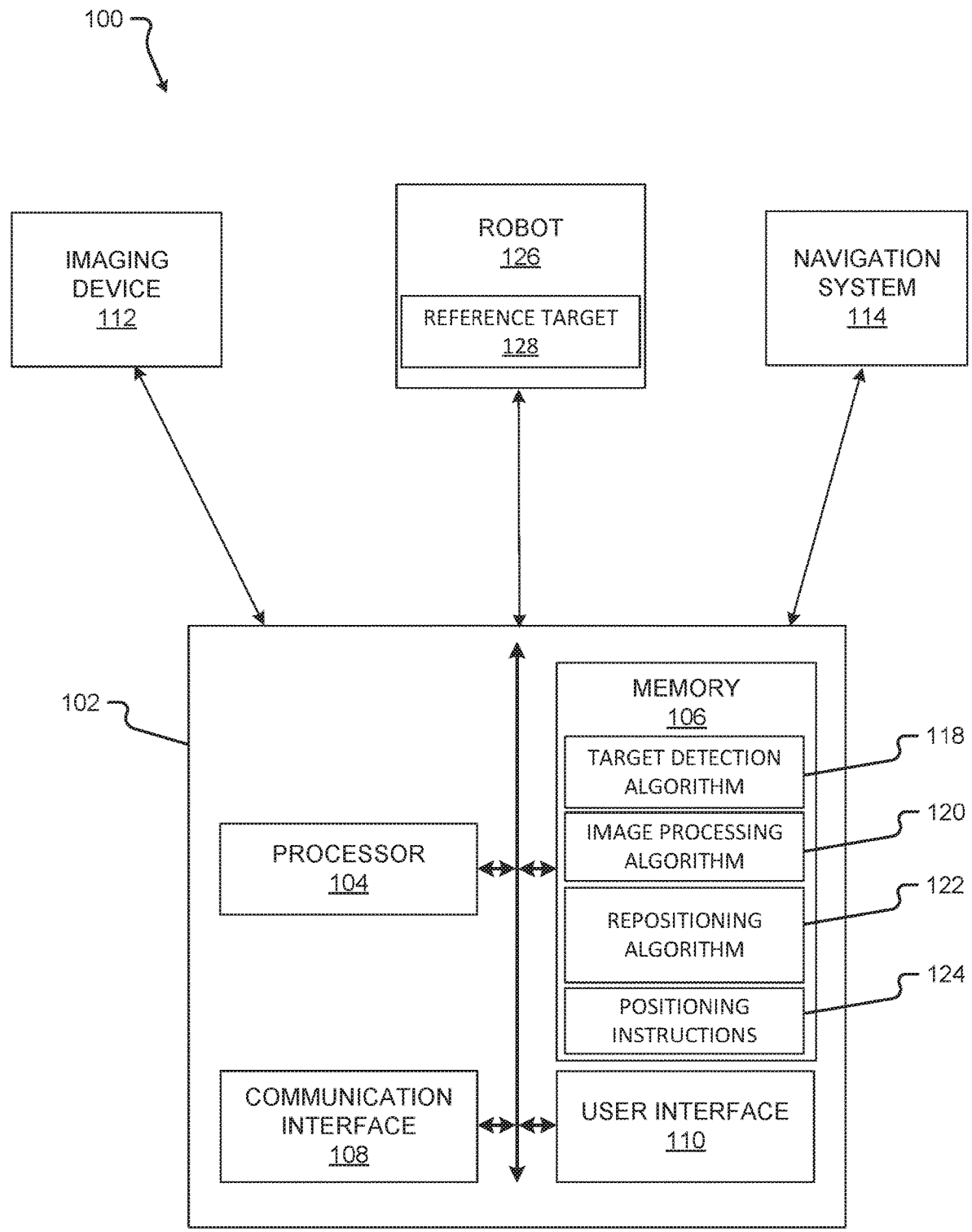
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Turning first to FIG. 1, a block diagram of a system 100 according to at least one embodiment of the present disclosure is shown. The system 100 may be used to process image data, execute a target detection algorithm, make a position and/or location determination, and/or carry out other aspects of one or more of the methods disclosed herein. The system 100 comprises a computing device 102, an imaging device 112, a navigation system 114, and/or a robot 126. The robot 126 may comprise a robotic arm that may be holding a reference target 128, or on which a reference target 128 may be disposed. The reference target 128 may be disposed on an end of the robotic arm in some examples, while in other examples the reference target 128 may be disposed on any portion of the robotic arm. In some embodiments, the reference target 128 may be useful for aligning, mapping, or otherwise registering a robotic coordinate space with a patient coordinate space.

The computing device 102 comprises a processor 104, a memory 106, a communication interface 108, and a user interface 110. Systems such as the system 100 according to other embodiments of the present disclosure may comprise more or fewer components than the system 100.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, and/or the navigation system 114.

The memory 106 may be or comprise RAM, DRAM, SDRAM, other solid-state memory, any memory described herein, or any other non-transitory memory for storing computer-readable data and/or instructions. The memory 106 may store information or data useful for completing any step of any of the methods 200, 400, 500 and/or 600 described herein. The memory 106 may store, for example, one or more target detection algorithms 118, one or more image processing algorithms 120, one or more position and/or location determination algorithms 122, and/or one or more positioning instructions 124. Such instructions or algorithms may, in some embodiments, be organized into one or more applications, modules, packages, layers, or engines. The algorithms and/or instructions may cause the processor 104 to manipulate data stored in the memory 106 and/or received from the imaging device 112, and/or the navigation system 114.

The computing device 102 may also comprise a communication interface 108. The communication interface 108 may be used for receiving image data or other information from an external source (such as the imaging device 112, the robot 126, and/or the navigation system 114), and/or for transmitting instructions, images, or other information to an external source (e.g., the navigation system 114, another computing device 102, and/or the robot 126). The communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, touchscreen, and/or any other device for receiving information from a user and/or for providing information to a user. The user interface 110 may be used, for example, to receive a user selection or other user input regarding first instructions configured to cause a robot to position a reference target; to receive a user selection or other user input regarding determining whether all, some, or none of a reference target is represented in the image data; to receive a user selection or other user input regarding determining whether all, some, or none of an anatomical element is represented in the image data; to receive user input regarding generating a repositioning requirement based on the imaging device, the reference target, and/or the anatomical element; to receive a user selection or other user input regarding second instructions for repositioning at least one of the imaging device and the reference target; to display the image data received from the imaging device 112; to display the first instructions; and/or to display second instructions for moving the imaging device 112 or causing the imaging device 112 to move, and/or configured to cause the reference target 128 to move (e.g., by causing the robotic arm supporting the reference target 128 to move). In some embodiments, the user interface 110 may be useful to allow a surgeon or other user to modify the first instructions, the second instructions, or other information displayed.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 is operable to image an anatomy of a patient (e.g., a spine region) to yield image data (e.g., image data depicting or corresponding to a spinal column of a patient). "Image data" as used herein refers to the data generated or captured by an imaging device, including in a machine-readable form, a graphical form, and in any other form. In various examples, the image data may correspond to a complete anatomical feature of a patient, or to a portion thereof (e.g., the entire spinal column of the patient or to a portion thereof). The imaging device 112 may be a device for obtaining X-ray images and/or image data (e.g., a fluoroscope, a CT scanner, or other X-ray machine), but may alternatively be a magnetic resonance imaging (MRI) scanner, an ultrasound scanner, an optical computed tomography scanner, or any other imaging device suitable for obtaining images of an anatomical element of a patient. The imaging device 112 may be, for example, a C-arm imaging device. The imaging device 112 may take an image from an underside of the patient, in which event the X-rays or other electromagnetic signals or waves pass through the patient first and then through the reference target 128 positioned above the patient.

During the surgical operation, the navigation system 114 may provide navigation for a surgeon and/or a surgical robot. In other embodiments, the surgical operation may not use a navigation system. The navigation system 114 may be any known or future navigation system, including, for example, the Medtronic StealthStation™ S8 surgical navigation system. In various embodiments, the navigation system 114 may be used to track a position of the imaging device 112 (or, more particularly, of a navigated tracker attached to the imaging device 112), and of the reference target 128 (which may be attached to the robot 126 or may be separate from the robot 126). The navigation system 114 may include a camera or other sensor(s) for tracking one or more reference markers, navigated trackers, or other objects within the operating room. The navigation system 114 may also track one or more reference targets in some embodiments. The navigation system 114 may include a display for displaying one or more images from an external source (e.g., the computing device 102, imaging device 112, or other source) or a video stream from the camera or other sensor of the navigation system 114. The navigation system 114 may be, for example, the same as or similar to a navigation system described by U.S. Pat. No. 7,366,562, entitled "Method and Apparatus for Surgical Navigation, filed Oct. 17, 2003, and assigned to Medtronic Navigation Inc., the entirety of which is hereby incorporated by reference herein.

Figure 2:
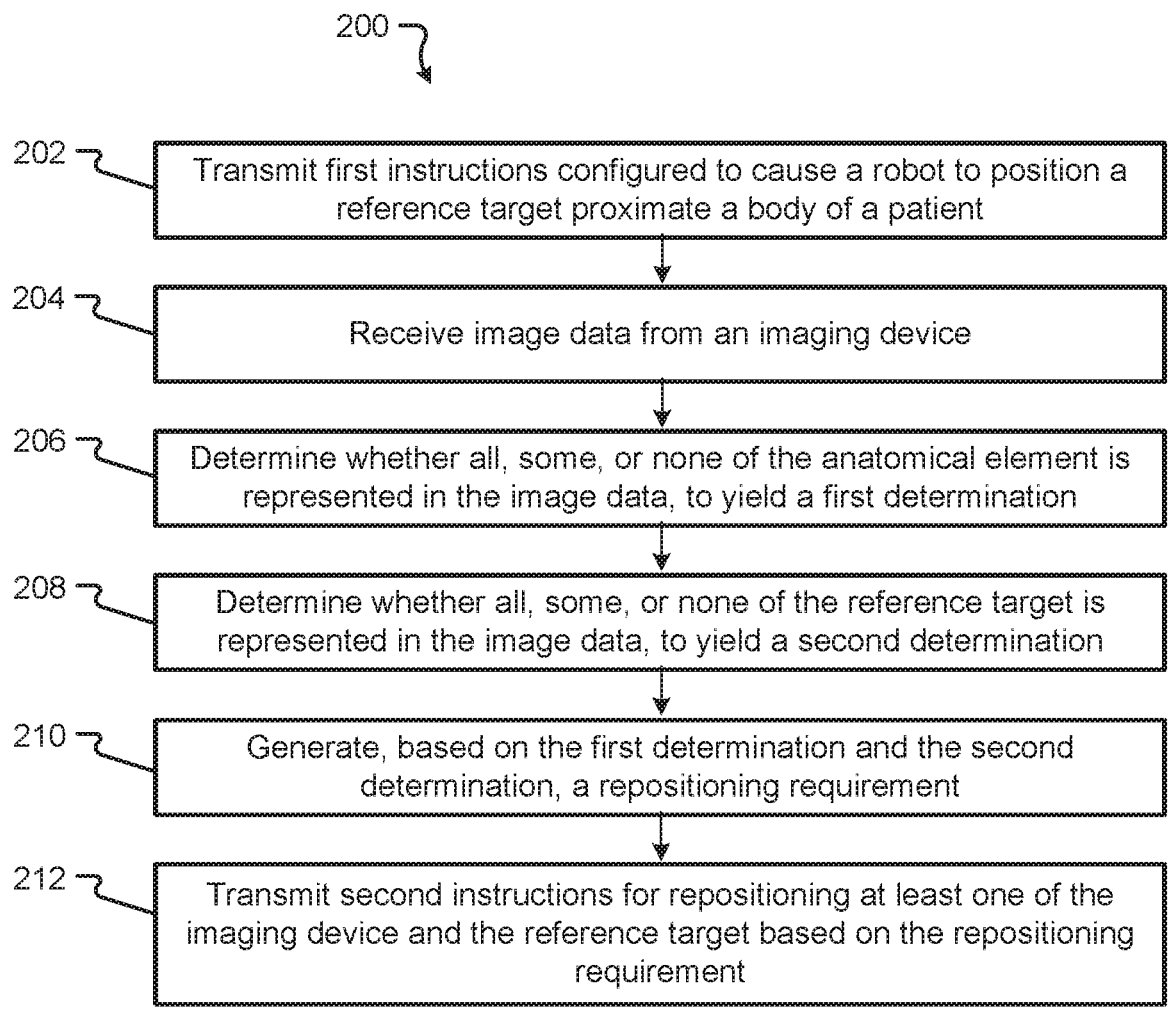
FIG. 2 is a flowchart of a method according to at least one embodiment of the present disclosure.

Turning now to FIG. 2, a method 200 for aligning an imaging device 112 in connection with a surgical procedure on an anatomical feature of a patient according to embodiments of the present disclosure may be executed in whole or in part on a computing device 102. The alignment is performed during initial setup for a surgical operation. The surgery may be performed by a surgical robot, a surgeon, or a combination of both.

The method 200 comprises transmitting positioning instructions 124 comprising first instructions configured to cause the robot 126 to position the reference target 128 proximate a body of a patient (step 202), and more specifically proximate a portion of the body of the patient containing an anatomical element that is the subject of the planned surgery. The reference target 128 may also be positioned directly on the patient. The reference target 128 may be or comprise one or more optical targets that can be detected in image data. In other embodiments, the reference target 128 may be navigation markers or spheres, and may be configured for detection by a navigation system such as the navigation system 114, which may be an optical (visual wavelength) navigation system, an infrared navigation system, an electromagnetic navigation system, or any other navigation system. The first instructions may be transmitted to the robot 126 from the communication interface 108 to cause the robot 126 to automatically position the reference target 128. In other examples, the first instructions may be displayed on the user interface 110, and a user may cause the robot 126 to move the robotic arm, and thus the reference target 128, based on the displayed first instructions. The first instructions may be based on a surgical plan and/or may be based on preoperative images taken prior to the procedure. Additionally or alternatively, the first instructions may be based on user-provided input regarding an observed location (or at least an estimated location based on one or more observations of the patient) of the anatomical feature that is the subject of the planned surgery.

The method 200 further comprises receiving image data from the imaging device 112 (step 204). The image data may, for example, be machine-readable and may be useful for displaying an image on a user interface 110 or elsewhere. The image data may correspond to (e.g., may contain data representing) the anatomical feature that is the subject of the planned surgery, which may be any anatomical element—for example, a spinal column or spinal element, an appendage, a cranial element, or the like. In some examples, the image data may comprise or correspond to a two-dimensional image. The image data may correspond to an image taken of the spinal column of the patient using an imaging device 112, such as an MRI scanner, a CT scanner, a fluoroscopy device, or another imaging device. In various embodiments, the image data may contain data for an entire spinal column of the patient or for a portion of the spinal column of the patient. The image data is generated by the imaging device 112, but may be received directly from the imaging device 112 or indirectly via any other source. The image data may be received via the communication interface 108. Processing of the image data may include applying the image processing algorithm 120 to the image data (or, alternatively, inputting the image data to the image processing algorithm 120), which algorithm 120 may apply one or more filters to the image data 300 to prepare the image data 300 for further processing. FIGS. 3A-3D provide a visual depiction of four different possible sets of image data 300.

The method 200 further comprises determining whether all, some, or none of an anatomical element is represented in the image data 300 to yield a first determination (step 206). The anatomical element 302, as shown in FIGS. 3A-3D, may be identified by executing the image processing algorithm 120 by the processor 104. The image processing algorithm 120 may, in some embodiments, use a neural network, machine learning, artificial intelligence, or the like, to process the image data 300. Identifying the anatomical element 302 may include segmenting the image data 300 and evaluating the resulting segments. In some embodiments, the image processing algorithm 120 may comprise a feature identification algorithm that identifies objects in the image data 300 and compares them to one or more known shapes to determine whether the identified objects correlate to a known shape and can therefore be identified as a known anatomical element 302. In other embodiments, the image processing algorithm 120 may be generated by a machine learning engine based on training data. The training data may be or comprise, for example, a plurality of images of anatomical features that have been marked so that the machine learning engine can identify correlations between different images of the same anatomical feature and thus learn to identify the anatomical feature in question.

In other embodiments, a surgeon or other user may identify the anatomical element 302 by providing one or more inputs via a user interface 110. In such embodiments, the identification of the anatomical element 302 may be based on the image data 300 and/or additional information obtained from the user.

Figure 3A:
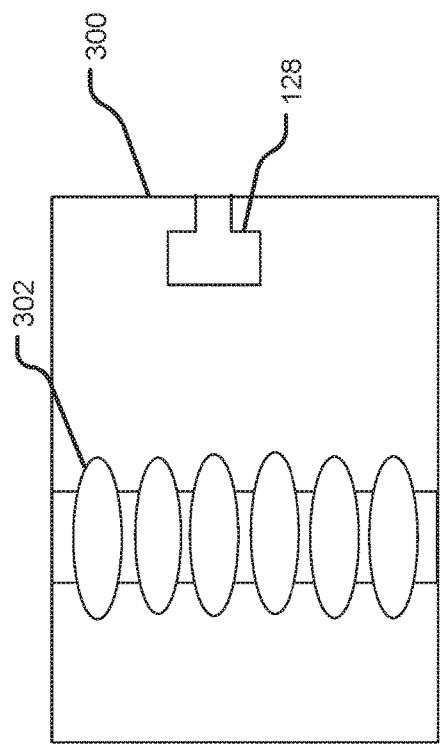
FIG. 3A is an image of an anatomical element and a reference target according to at least one embodiment of the present disclosure.
Figure 3B:
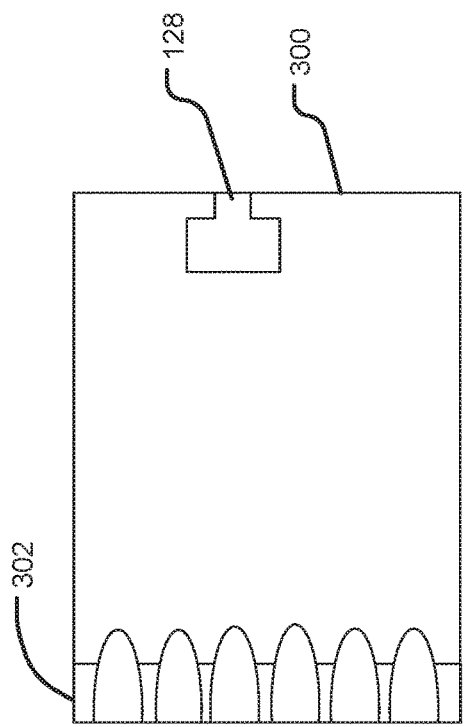
FIG. 3B is an image of an anatomical element and a portion of a reference target according to at least one embodiment of the present disclosure.
Figure 3C:
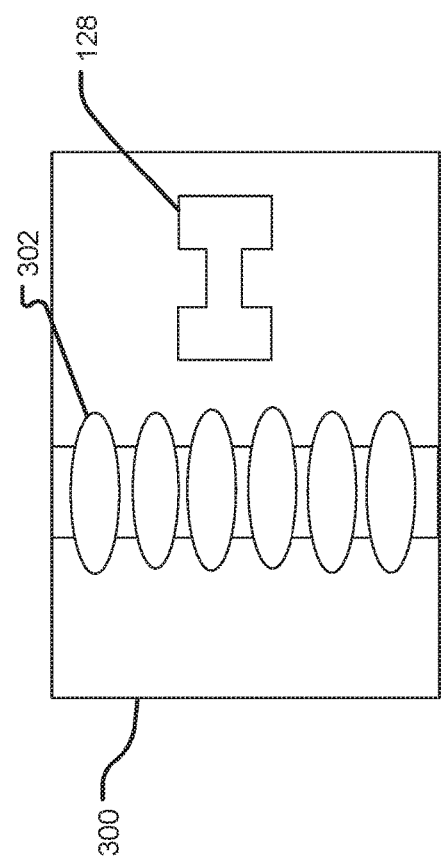
FIG. 3C is an image of a portion of an anatomical element and a reference target according to at least one embodiment of the present disclosure.
Figure 3D:
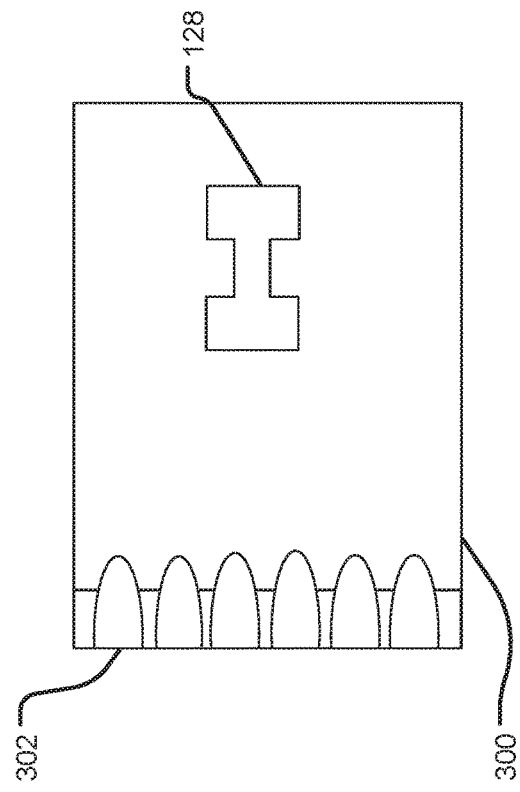
FIG. 3D is an image of a portion of an anatomical element and some of a reference target according to at least one embodiment of the present disclosure.

The first determination corresponds to whether some, all, or none of the anatomical element 302 is represented in the image data 300. The first determination also corresponds to whether the imaging device 112 is misaligned. For example, if some or none of the anatomical element 302 is not represented in the image data 300, as shown in FIGS. 3C and 3D, then the imaging device 112 is not properly aligned. Conversely, if all of the anatomical element 302 is in the image data 300, as shown in FIGS. 3A and 3B, then the imaging device 112 is properly aligned.

The method 200 further comprises determining whether all, some, or none of the reference target 128 is represented in the image data 300 to yield a second determination (208). The reference target 128 may be identified using a target detection algorithm 118 executed by the processor 104. In some embodiments, the algorithm 118 may detect the reference target 128 by comparing the image data 300 to preoperative image data with or without a reference target 128. In other embodiments, the algorithm 118 may identify one or more shapes corresponding to the reference target 128 in the image data 300 based on input to the algorithm 118 regarding the shape(s) of the reference target. For example, the algorithm 118 may receive input (e.g., from a user via the user interface 110) that the reference target 128 is a square and may search for a square or substantially square shape in the image data 300. In other embodiments, the shape may include, but is not limited to, a circle, an oval, a start, a pentagon, or the like.

In still other embodiments, the target detection algorithm 118 may search the image data 300 for data that corresponds to a readily distinguishable objects included in the reference target 128. Thus, for example, if a reference target 128 is known to comprise an oblong shape, then the target detection algorithm 118 may analyze the image data 300 to determine whether some or all of the oblong shape is represented in the image data 300. If the oblong shape is represented in the image data 300, the target detection algorithm 118 may determine that the entire reference target 128 is in the image data 300. If some of the oblong shape is in the image data 300, then the target detection algorithm 118 may determine that only a portion of the reference target 128 is in the image data 300. And, if the oblong shape is not represented in the image data 300, the target detection algorithm 118 may determine that the reference target 128 does not appear in the image data 300.

Similarly, in other embodiments, if a reference target 128 is known to comprise four spheres mounted to a frame, then the target detection algorithm 118 may analyze the image data 300 to determine whether four spheres are represented in the image data 300. If all four spheres are represented in the image data 300, the target detection algorithm 118 may determine that the entire reference target 128 is in the image data 300. If at least one but fewer than four spheres are in the image data 300, then the target detection algorithm 118 may determine that only a portion of the reference target 128 is in the image data 300. And, if no spheres are represented in the image data 300, the target detection algorithm 118 may determine that the reference target 128 does not appear in the image data 300.

In still other embodiments, a surgeon or other user may identify the reference target 128 in the image data 300 by providing one or more inputs via a user interface 110. In such embodiments, the identification of the reference target 128 may be based on the image data and/or additional information obtained from user.

The second determination corresponds to whether some, all, or none of the reference target 128 is represented in the image data 300. The second determination also corresponds to whether the reference target 128 is misaligned. For example, if less than all of the reference target 128 is represented in the image data 300, as shown in FIGS. 3B and 3D, then the reference target 128 is not properly aligned. Conversely, if all of the reference target 128 is represented in the image data 300, as shown in FIGS. 3A and 3C, then the reference target 128 is properly aligned.

The method 200 also comprises generating a repositioning requirement based on the first determination and the second determination (step 210). The repositioning requirement may be calculated using the repositioning algorithm 122. The algorithm 122 determines if the imaging device 112 and/or the reference target 128 requires repositioning based on whether the imaging device 112 and/or the reference target 128 are misaligned, and if so, calculates a new position for the imaging device 112 and/or the reference target 128. The repositioning requirement may be based on a geometric comparison of a position of the imaging device 112 (which is movable), the anatomical element (which is stationary), and a position of the reference target 128 (which is movable).

The repositioning requirement may be based at least in part on a portion of the anatomical element 302 or the reference target 128 that is not represented in the image data 300. For example, a portion of the anatomical element 302 (e.g., a spine region) in FIGS. 3C and 3D is not represented in the image data 300. Based on a portion of the anatomical element 302 that is represented in the image data 300, a direction or predicted position of the portion of the anatomical element 302 not represented in the image 300 can be determined based on the known portion of the anatomical element 302 that is represented in the image data 300. For example, in FIGS. 3C and 3D, the portion of the anatomical element 302 not represented in the image data 300 is to a left side of a frame of the image data 300 and thus, the predicted position of the portion not represented in the image data 300 would be to the left of the frame. The algorithm 122 can calculate a needed change in position or new position for the imaging device 112 based on the direction or predicted position of the portion of the anatomical element 302 not represented in the image data 300.

In another example, generating the repositioning requirement includes determining a needed change in position or new position of the reference target 128. For example, a portion of the reference target 128 in FIGS. 3B and 3D is not represented in the image data 300. Based on the portion of the reference target 128 that is represented in the image data 300, a direction or predicted position of the portion not represented in the image data 300 can be generated. For example, in FIGS. 3B and 3D, the portion of the reference target 128 not represented in the image data 300 is to a right side of a frame of the image data 300 and thus, the predicted position of the portion not represented in the image data 300 would be to the right of the frame. As a result, movement of the reference target 128 to the left would enable the reference target 128 to be positioned entirely within the image data 300. The algorithm 122 can calculate the repositioning requirement of the reference target 128 based on the predicted position of the portion of the reference target 128 not represented in the image data 300. In some embodiments, the repositioning requirement may reflect a needed change in position of the reference target 128 toward the center of an image represented by the image data 300.

The repositioning requirement may correspond to both the reference target 128 and the imaging device 112 when neither the reference target 128 nor the anatomical element 302 are identified or visible in the image data 300 or, as shown in FIG. 3D, when the image data 300 lacks a portion of both the reference target 128 and the anatomical element 302. In such circumstances, the repositioning requirement identifies a needed change in position or new position for both the imaging device 112 and the reference target 128.

The method 200 further comprises transmitting positioning instructions 124 comprising second instructions for repositioning the imaging device 112 and/or the reference target 128 based on the repositioning requirement (step 212). As explained above, the repositioning requirement may identify a needed change in position or new position for the imaging device 112 and/or the reference target 128. The second instructions may be configured to reposition the imaging device 112 based on the repositioning requirement. Additionally or alternatively, the second instructions may be configured to reposition the reference target 128 based on the repositioning requirement. In some embodiments, the second instructions are configured to reposition the imaging device 112 first, until all of the anatomical element 302 is represented in the image data 300, and then to reposition the reference target 128 until all of the reference target 128 is included in the image data 300. In other embodiments, the second instructions are configured to reposition the reference target 128 first, then the imaging device 112.

The repositioning of the imaging device 112 and/or of the reference target 128 may occur iteratively by repeating the steps 204 through 212 until an entirety of both the anatomical element 302 and the reference target 128 is represented in the image data.

If an entirety of both the anatomical element 302 and the reference target 128 are represented in the image data 300, then no repositioning requirement is calculated and alignment of the imaging device 112 and the reference target 128 is complete.

In various examples, the second instructions may be machine readable to cause both the imaging device 112 to automatically move and/or to cause the robot 126 to automatically move the reference target 128. In other examples, the second instructions may comprise both human-readable instructions displayed on the user interface 110 instructing the user to move (and, in some embodiments, how to move) the imaging device 112, and machine-readable instructions to cause the robot 126 to automatically move the reference target 128. In still other examples, the second instructions may comprise both machine-readable instructions to cause the imaging device 112 to automatically move and human-readable instructions displayed on the user interface 110 instructing the user to move (and, in some embodiments, how to move) the robot 126 and/or the reference target 128. In still further examples, the second instructions may comprise human-readable instructions displayed on the user interface 110 instructing the user to move (and, in some embodiments, how to move) the imaging device 112 and the robot 126 and/or the reference target 128.

As may be appreciated based on the foregoing disclosure, if one of the imaging device 112 and the reference target 128 is fully represented within the image data 300, then the second instructions may not include instructions for moving the one of the imaging device 112 and the reference target 128. On the other hand, if for example the anatomical element 302 is not fully represented in the image data 300 and the reference target 128 is fully represented in the image data 300, but movement of the imaging device 112 to capture the entirety of the anatomical element 302 may or will cause some or all of the reference target 128 to not be represented in the image data 300, then the second instructions may include instructions for moving both the imaging device 112 and the reference target 128.

Figure 4:
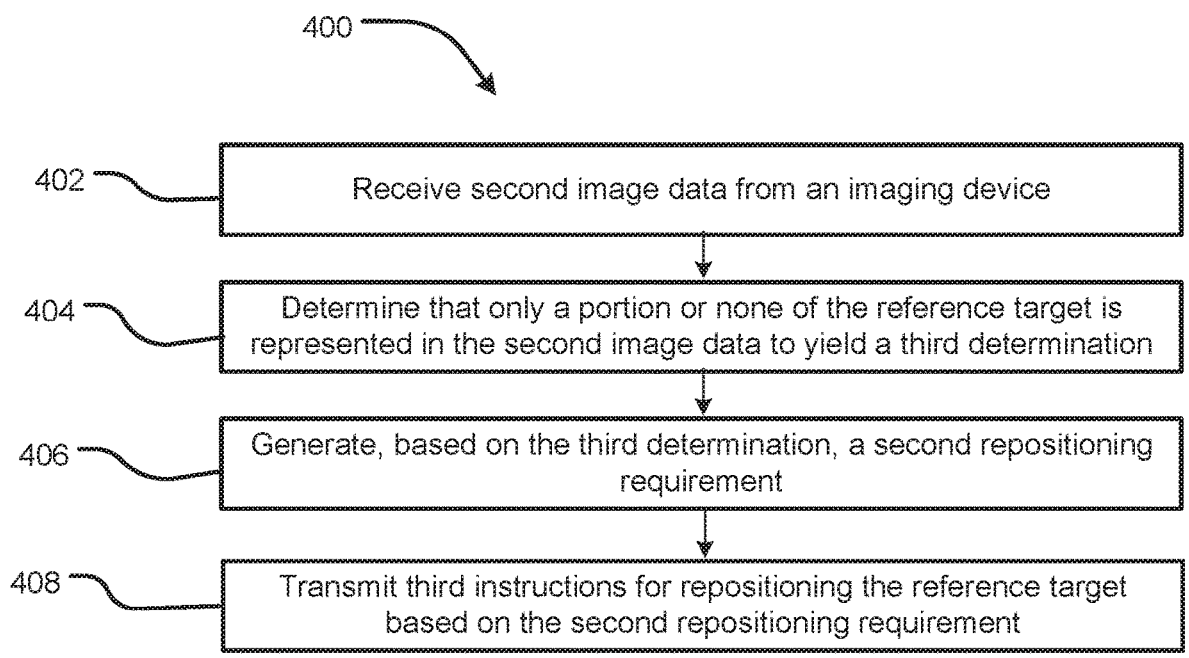
FIG. 4 is another flowchart of a method according to at least one embodiment of the present disclosure.

Turning now to FIG. 4, a method 400 of further aligning the reference target 128 comprises receiving or obtaining a second set of image data (step 402). The received second image data may be received or obtained in the same manner as or in a similar manner to the image data received in step 204 of the method 200. The second image data may correspond to the anatomical feature 302 that is the subject of the planned surgery, which may be any anatomical element—for example, a spinal column or spinal element, an appendage, a cranial element, or the like. In some examples, the second image data may comprise or correspond to a two-dimensional image. The second image data may correspond to a second image taken of the spinal column of the patient using the imaging device 112, such as an MRI scanner, a CT scanner, a fluoroscopy device, or another imaging device. In various embodiments, the second image data may contain data for an entire spinal column of the patient or for a portion of the spinal column of the patient. The second image data is generated by the imaging device 112, but may be received directly from the imaging device 112 or indirectly via any other device or system (e.g., a database, the cloud or another network), and may be received via the communication interface 108. Processing of the second image data may include applying the image processing algorithm 120, which may apply one or more filters to the second image data to prepare the second image data for further processing.

The method 400 also comprises determining that only a portion or none of the reference target 128 is not represented within the second image data to yield a third determination (step 404). The step 404 may be the same as or similar to the step 208 of the method 200. The reference target 128 can be identified using the target detection algorithm 118. For example, in some embodiments, the algorithm 118 may detect the reference target 128 by comparing the second image data to preoperative image data without a reference target 128. In other embodiments, the algorithm 118 may identify a shape corresponding to the reference target 128 in the second image data based on input to the algorithm 118 regarding the shape. For example, the algorithm 118 may receive input (e.g., from a user via the user interface 110) that the reference target 128 is a square and may search for a square or substantially square shape in the second image data. In other embodiments, the shape may include, but is not limited to, a circle, an oval, a start, a pentagon, or the like.

In still other embodiments, the target detection algorithm 118 may search the second image data for data that corresponds to a readily distinguishable objects included in the reference target 128. Thus, for example, if a reference target 128 is known to comprise an oblong shape, then the target detection algorithm 118 may analyze the image data 300 to determine whether some or all of the oblong shape is represented in the image data 300. If the oblong shape is represented in the image data 300, the target detection algorithm 118 may determine that the entire reference target 128 is in the image data 300. If some of the oblong shape is in the image data 300, then the target detection algorithm 118 may determine that only a portion of the reference target 128 is in the image data 300. And, if the oblong shape is not represented in the image data 300, the target detection algorithm 118 may determine that the reference target 128 does not appear in the image data 300.

Similarly, in other embodiments, if a reference target 128 is known to comprise four navigation spheres mounted to a frame, then the target detection algorithm 118 may analyze the image data to determine whether four navigation spheres are represented in the image data. If all four navigation spheres are represented in the data, the target detection algorithm 118 may determine that the entire reference target 128 is in the image. If at least one but fewer than four navigation spheres are in the image, then the target detection algorithm 118 may determine that only a portion of the reference target 128 is in the image. And, if no navigation spheres are represented in the data, the target detection algorithm 118 may determine that the reference target 128 does not appear in the image.

In still other embodiments, a surgeon or other user may identify the reference target 128 by providing one or more inputs via a user interface 110. In such embodiments, the identification of the reference target 128 may be based on the second image data and/or additional information obtained from user.

The third determination corresponds to whether only a portion or none of the reference target 128 is represented in the second image data and whether the reference target 128 is misaligned. If the reference target 128 is not entirely represented in the second image data, as shown in FIGS. 3B and 3D, then the reference target 128 is not properly aligned.

The method 400 also comprises generating, based on the third determination, a second repositioning requirement (step 406). The step 406 may be the same as or similar to the step 210 of the method 200. The second repositioning requirement can be generated using the repositioning algorithm 122 (e.g., in one or more of the ways described above with respect to the step 210 of the method 200). The second repositioning requirement includes repositioning the reference target 128 in a direction of a portion of the reference target 128 not represented in the image data 300. For example, a portion of the reference target 128 in FIGS. 3B and 3D are not represented in the image data 300. Based on a portion of the reference target 128 that is represented in the image data, a direction or predicted position of the portion not represented in the image data 300 can be generated based on the portion of the reference target 128 that is represented in the image data 300. For example, in FIGS. 3B and 3D, the portion of the reference target 128 not represented in the image data 300 is to a right side of a frame of the image data 300 and thus, the predicted position of the portion not represented in the image data 300 would be to the right of the frame. The algorithm 122 can calculate the repositioning requirement of the reference target 128 based on the predicted position of the portion of the reference target 128 not represented in the image data 300, and/or based on a change in position of the reference target 128 that would place the reference target 128 closer to the center of an image represented by the second image data.

The method 400 further comprises transmitting positioning instructions 124 comprising third instructions for repositioning the reference target 128 (step 408). The step 408 may be the same as or similar to the step 212 of the method 200. In some examples, the third instructions may be configured to automatically cause the robot 126 to reposition the reference target 128. In other embodiments, the third instructions may be displayed on a user interface 110 or other device so that a user can manually reposition the reference target 128 (and the robotic arm to which the reference arm 128 is attached). In various embodiments, the second instructions are configured to reposition the reference target 128 toward a center of an image represented by the second image data.

The method 400 may be repeated until the reference target 128 is properly aligned, as indicated by identification of the reference target 128 in its entirety in the second image data or subsequent image data.

Figure 5:
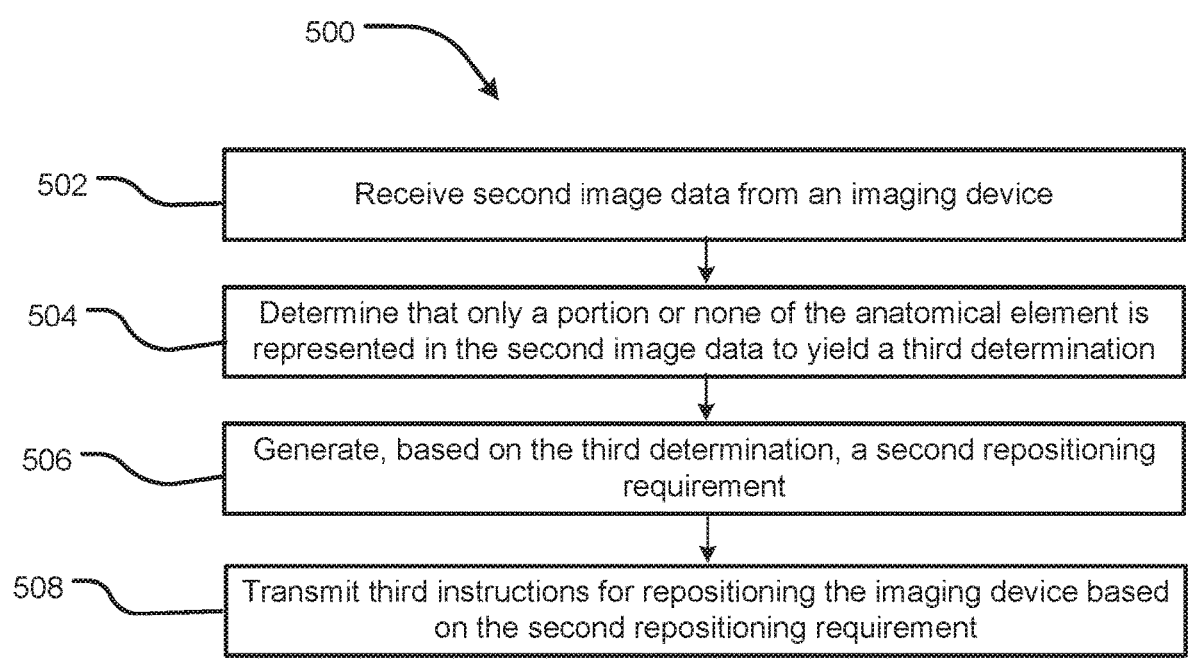
FIG. 5 is another flowchart of a method according to at least one embodiment of the present disclosure.

Turning now to FIG. 5, a method 500 of further aligning the imaging device 112 includes receiving or obtaining second image data (step 502). The receiving or obtaining of the second image data may be accomplished in the same manner as or in a similar manner to step 402 of the method 400 and/or step 204 of the method 200. The second image data may correspond to the anatomical feature 302 that is the subject of the planned surgery, which may be any anatomical element—for example, a spinal column or spinal element, an appendage, a cranial element, or the like. In some examples, the second image data may comprise or correspond to a two-dimensional image. The second image data may correspond to a second image taken of the spinal column of the patient using the imaging device 112, such as an MM scanner, a CT scanner, a fluoroscopy device, or another imaging device. In various embodiments, the second image data may contain data for an entire spinal column of the patient or for a portion of the spinal column of the patient.

The second image data is generated by the imaging device 112, but may be received directly from the imaging device 112 or indirectly via any other device or system (e.g., a database, the cloud or another network), and may be received via the communication interface 108. Processing of the second image data may include applying the image processing algorithm 120, which may apply one or more filters to the second image data to prepare the second image data for further processing.

The method 500 also comprises determining that only a portion or none of the anatomical element 302 is represented in the second image data 300 to yield a third determination (step 504). The step 504 may be the same as or similar to the step 206 of the method 200. As in the step 206 described above, the anatomical element 302, as shown in FIGS.

3A-3D, may be identified by executing the image processing algorithm 120 using the processor 104. The image processing algorithm 120 may, in some embodiments, use a neural network, machine learning, artificial intelligence, or the like, to process the image data. Identifying the anatomical element 302 may include segmenting the image data and evaluating the resulting segments. In some embodiments, the image processing algorithm 120 may comprise a feature identification algorithm that identifies objects in the image data and compares them to one or more known shapes to determine whether the identified objects correlate to a known shape and can therefore be identified as a known anatomical element 302. In other embodiments, the image processing algorithm 120 may be generated by a machine learning engine based on training data. The training data may be or comprise, for example, a plurality of images of anatomical features that have been marked so that the machine learning engine can identify correlations between different images of the same anatomical feature and thus learn to identify the anatomical feature in question.

In other embodiments, a surgeon or other user may identify the anatomical element 302 by providing one or more inputs via a user interface 110. In such embodiments, the identification of the anatomical element 302 may be based on the image data and/or additional information obtained from the user.

The third determination corresponds to whether only a portion or none of the anatomical element 302 is represented in the image data 300. The third determination also corresponds to whether the imaging device 112 is misaligned. If some or none of the anatomical element 302 is not represented in the image data 300, as shown in FIGS. 3C and 3D, then the imaging device 112 is not properly aligned.

The method 500 also comprises generating, based on the third determination, a second repositioning requirement (step 506). The step 506 may be the same as or similar to the step 210 of the method 200. The second repositioning requirement can be generated using the repositioning algorithm 122 (e.g., in one or more of the ways described above with respect to the step 210 of the method 200). The second repositioning requirement may be based on a portion of the anatomical element 302 or the reference target 128 that is not represented in the image data. For example, a portion of the anatomical element 302 (e.g., a spine region) in FIGS. 3C and 3D is not represented in the second image data. Based on a portion of the anatomical element 302 that is represented in the second image data, a direction or predicted position of the portion of the anatomical element 302 not represented in the second image can be generated based on the known portion of the anatomical element 302 that is represented in the second image data. For example, in FIGS. 3C and 3D, the portion of the anatomical element 302 not represented in the second image data is to a left side of a frame of the second image data and thus, the predicted position of the portion not represented in the second image data would be to the left of the frame. The algorithm 122 can calculate the repositioning requirement of the imaging device 112 based on the direction or predicted position of the portion of the anatomical element 302 not represented in the second image data.

The method 500 further comprises transmitting positioning instructions 124 comprising third instructions for repositioning the imaging device based on the second repositioning requirement (step 508). The step 508 may be the same as or similar to the step 212 of the method 200. In some examples, the third instructions may be configured to automatically cause the imaging device 112 to be repositioned. In other embodiments, the third instructions may be displayed on a user interface 110 or other device so that a user can manually reposition the imaging device 112. In various embodiments, the third instructions are configured to reposition the imaging device 112 based on a portion of the anatomical element 302 not represented in the second image data, as described above with respect to step 210.

The method 500 may be repeated until the imaging device 112 is properly aligned, as indicated by identification of the anatomical element 302 in its entirety in the second image data or subsequent image data.

Figure 6:
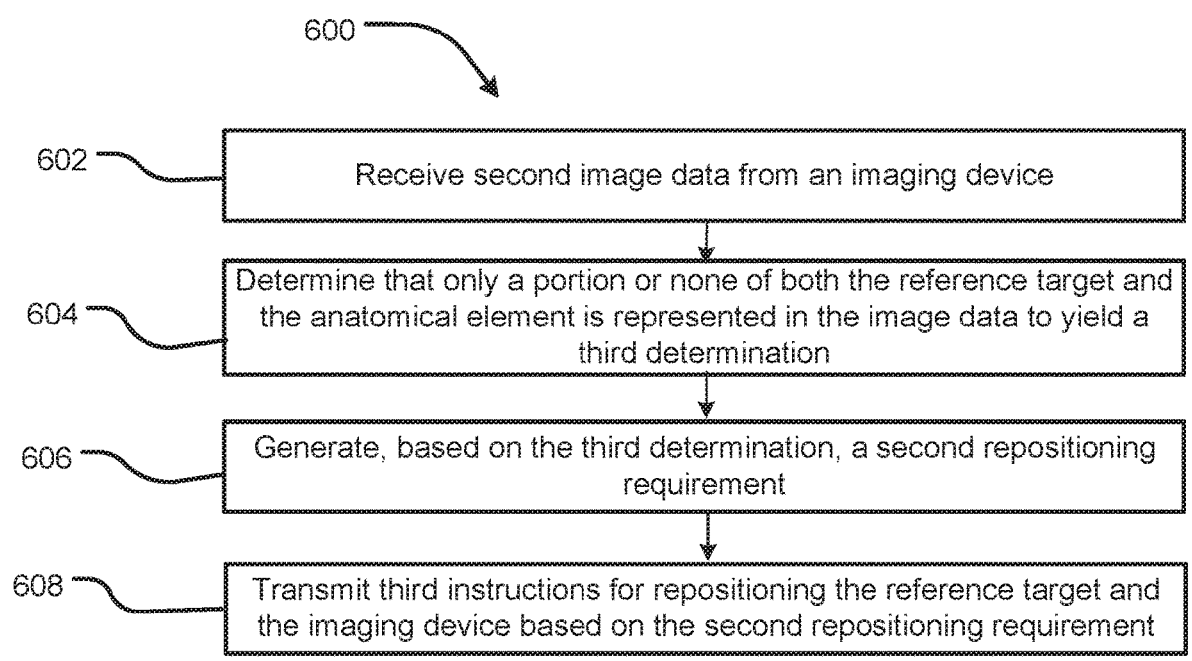
FIG. 6 is another flowchart of a method according to at least one embodiment of the present disclosure.

Turning now to FIG. 6, a method 600 of further aligning the imaging device 112 and the reference target 128 includes receiving or obtaining second image data (step 602). The receiving or obtaining the second image data may be accomplished in the same manner as or in a similar manner to step 502 of the method 500, step 402 of the method 400, and/or step 204 of the method 200. The second image data may correspond to the anatomical feature 302 that is the subject of the planned surgery, which may be any anatomical element—for example, a spinal column or spinal element, an appendage, a cranial element, or the like. In some examples, the second image data may comprise or correspond to a two-dimensional image. The second image data may correspond to a second image taken of the spinal column of the patient using the imaging device 112, such as an MM scanner, a CT scanner, a fluoroscopy device, or another imaging device. In various embodiments, the second image data may contain data for an entire spinal column of the patient or for a portion of the spinal column of the patient. The second image data is generated by the imaging device 112, but may be received directly from the imaging device 112 or indirectly via any other device or system (e.g., a database, the cloud or another network), and may be received via the communication interface 108. Processing of the second image data may include applying the image processing algorithm 120, which may apply one or more filters to the second image data to prepare the second image data for further processing.

The method 600 also comprises determining that only a portion or none of both the reference target 128 and the anatomical element 302 is represented in the second image data to yield a third determination (step 604). A lack of some or all of the anatomical element 302 can be identified using the image processing algorithm 120 (e.g., in one or more of the ways described above with respect to step 206 of the method 200 or step 504 of the method 500) and a lack of some or all of the reference target 128 can be identified using the target detection algorithm 118 (e.g., in one or more of the ways described above with respect to step 208 of the method 200 and/or step 404 of the method 400).

The third determination corresponds to whether only a portion or none of both the anatomical element 302 and the reference target 128 is represented in the second image data. The third determination also corresponds to whether the imaging device 112 and the reference target 128 is misaligned. If only a portion or none of both the anatomical element 302 and the reference target 128 is represented in the second image data, as shown in FIG. 3D, then the imaging device 112 and the reference target 128 are not properly aligned.

The method 600 also comprises generating, based on the third determination, a second repositioning requirement (step 606). The step 606 may be the same as or similar to the step 210 of the method 200. For example, the second repositioning requirement can be generated using the repositioning algorithm 122. As another example, the second repositioning requirement may be based on a geometric comparison of a position of the imaging device 112 (which is movable), the anatomical element (which is stationary), and a position of the reference target 128 (which is movable).

As yet another example, the second repositioning requirement may correspond to both the reference target 128 and the imaging device 112 when neither the reference target 128 nor the anatomical element 302 are identified or visible in the second image data or, as shown in FIG. 3D, when the second image data lacks a portion of both the reference target 128 and the anatomical element 302.

The method 600 further comprises transmitting positioning instructions 124 comprising third instructions for repositioning the imaging device 112 and/or the reference target 128 based on the repositioning requirement (step 608). The step 608 may be the same as or similar to the step 212 of the method 200. In some embodiments, the third instructions are configured to reposition the imaging device 112 first, until all of the anatomical element 302 is represented in the second image data, and then to reposition the reference target 128 until all of the reference target 128 is included in the second image data. In other embodiments, the third instructions are configured to reposition the reference target 128 first, then the imaging device 112.

In various examples, the third instructions may be machine readable to cause both the imaging device 112 to automatically move and/or to cause the robot 126 to automatically move the reference target 128. In other examples, the third instructions may comprise both human-readable instructions displayed on the user interface 110 instructing the user to move (and, in some embodiments, how to move) the imaging device 112, and machine-readable instructions to cause the robot 126 to automatically move the reference target 128. In still other examples, the third instructions may comprise both machine-readable instructions to cause the imaging device 112 to automatically move and human-readable instructions displayed on the user interface 110 instructing the user to move (and, in some embodiments, how to move) the robot 126 and/or the reference target 128. In still further examples, the third instructions may comprise human-readable instructions displayed on the user interface 110 instructing the user to move (and, in some embodiments, how to move) the imaging device 112 and the robot 126 and/or the reference target 128.

The method 600 may be repeated until the imaging device 112 and the reference target 128 are properly aligned, as indicated by identification of the reference target 128 and the anatomical element 302 in their entirety in the second image data or subsequent image data.

The methods and systems described provide an efficient method for aligning an imaging device for robotic surgery. Further, the methods and systems described herein reduce the amount of imaging needed for each iteration, thereby reducing the amount of radiation to which a patient is exposed. The method is simple to implement and portions of or the entire method may be automated, thereby reducing initial setup time and overall operation time.

As may be appreciated based on the foregoing disclosure, the present disclosure encompasses methods with fewer than all of the steps identified in FIGS. 2 and 4-6 (and the corresponding description), as well as methods that include steps from more than one of FIGS. 2 and 4-6 (and the corresponding description) and methods that include one or more steps disclosed herein in combination with one or more steps not disclosed herein.

One or more aspects of the present disclosure may be the same as or similar to one or more corresponding aspects described in U.S. patent application Ser. No. 16/854,011, filed contemporaneously herewith by the same applicant, entitled "System and Method for Positioning an Imaging Device" and naming the same inventor as the present application, which is hereby incorporated herein by reference in its entirety.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for aligning a reference target and an imaging device for robotic surgery, comprising:
   a processor; and
   a memory storing instructions for execution by the processor that, when executed, cause the processor to:
   transmit first instructions configured to cause a robot to position a reference target proximate a body of a patient,
   receive image data from the imaging device,
   determine, using an image processing algorithm, an amount of an anatomical element that is represented in the image data, to yield a first determination,
   determine, using a target detection algorithm, an amount of the reference target that is represented in the image data, to yield a second determination,
   obtain a comparison of a position of the imaging device, a position of the anatomical element, and a position of the reference target,
   generate, based on the first determination, the second determination, and the comparison, a repositioning requirement for the imaging device, the reference target, or both,
   transmit second instructions for repositioning at least one of the imaging device and the reference target based on the repositioning requirement, receive second image data,
determine, using the image processing algorithm, that the amount of the anatomical element that is represented in the second image data comprises less than all of the anatomical element to yield a third determination,
generate, based on the third determination, a second repositioning requirement,
transmit third instructions for repositioning the imaging device based on the second repositioning requirement,
compare the image data to one or more known shapes,
determine, based on the comparison of the image data to the one or more known shapes, that an object in the image data correlates to a known shape of the anatomical element, and
identify the object as the anatomical element in response to determining that the object in the image data correlates to the known shape of the anatomical element, wherein the third instructions are configured to cause automatic repositioning of the imaging device.

2. The system of claim 1, wherein the image processing algorithm uses a neural network.

3. The system of claim 1, wherein the imaging device is a fluoroscopy device.

4. The system of claim 1, wherein the memory further includes instructions that, when executed, cause the processor to:
determine, using the target detection algorithm, that the amount of the reference target that is represented in the second image data comprises less than all of the reference target to yield the third determination,
generate, based on the third determination, a third repositioning requirement, and
transmit fourth instructions for repositioning the reference target based on the third repositioning requirement.

5. The system of claim 4, wherein the fourth instructions are configured to reposition the reference target toward a center of an image represented by the second image data.

6. The system of claim 1, wherein the third instructions for repositioning the imaging device further comprise instructions for repositioning the imaging device in a direction of a portion of the anatomical element not represented in the second image data.

7. The system of claim 1, wherein the memory further includes instructions that, when executed, cause the processor to:
determine, using the image processing algorithm and the target detection algorithm, that the amount of the reference target that is represented in the image data comprises less than all of the reference target and the amount of the anatomical element that is represented in the image data comprises less than all of the anatomical element to yield a fourth determination,
generate, based on the fourth determination, a third repositioning requirement, and
transmit fourth instructions for repositioning the reference target and the imaging device based on the third repositioning requirement.

8. The system of claim 1, wherein the anatomical element corresponds to a vertebral anatomy.

9. A method of aligning an imaging device and a reference target for robotic surgery, comprising:
causing a robot to position a reference target proximate a body of a patient;
receiving image data from the imaging device;
determining, using an image processing algorithm, an amount of an anatomical element that is represented in the image data, to yield a first determination;
determining, using a target detection algorithm, an amount of the reference target that is represented in the image data, to yield a second determination;
obtaining a comparison of a position of the imaging device, a position of the anatomical element, and a position of the reference target;
generating, based on the first determination, the second determination, and the comparison, a repositioning requirement for the imaging device, the reference target, or both;
transmitting second instructions for repositioning at least one of the imaging device and the reference target based on the repositioning requirement;
receiving second image data;
determining, using the image processing algorithm, that the amount of the anatomical element that is represented in the second image data comprises less than all of the anatomical element to yield a third determination;
generating, based on the third determination, a second repositioning requirement;
transmitting third instructions for repositioning the imaging device based on the second repositioning requirement;
comparing the image data to one or more known shapes;
determining, based on the comparison of the image data to the one or more known shapes, that an object in the image data correlates to a known shape of the anatomical element; and
identifying the object as the anatomical element in response to determining that the object in the image data correlates to the known shape of the anatomical element, wherein the third instructions are configured to automatically cause repositioning of the imaging device.

10. The method of claim 9, further comprising:
determining, using the target detection algorithm, that the entire reference target is represented in the second image data.

11. The method of claim 9, further comprising:
determining, using the target detection algorithm, that the amount of the reference target that is represented in the second image data comprises less than all of the reference target to yield the third determination;
generating, based on the third determination, a third repositioning requirement; and
transmitting fourth instructions for repositioning the reference target based on the third repositioning requirement.

12. The method of claim 11, wherein the third instructions for repositioning the reference target further comprise repositioning the reference target toward a center of an image represented by the second image data.

13. The method of claim 9, wherein the third instructions for repositioning the imaging device comprise repositioning the imaging device in a direction of a portion of the anatomical element not represented in the second image data.

14. The method of claim 9, further comprising:
determining, using the image processing algorithm and the target detection algorithm, the amount of the reference target that is represented in the image data comprises less than all of the reference target and the amount of the anatomical element that is represented in the image data comprises less than all of the anatomical element to yield a fourth determination;

generating, based on the fourth determination, a third repositioning requirement; and transmitting fourth instructions for repositioning the reference target and the imaging device based on the third repositioning requirement.

15. The method of claim 9, wherein the imaging device is a fluoroscopy device.

16. A system for aligning an imaging device and a reference target for surgery, comprising:

at least one communication interface for communicating with the imaging device and a robot supporting the reference target with a robotic arm;

a processor; and a memory storing instructions for execution by the processor that, when executed, cause the processor to:

receive image data, via the communication interface, from the imaging device, determine, using an image processing algorithm, an amount of an anatomical element that is represented in the image data, to yield a first determination, determine, using a target detection algorithm, an amount of the reference target that is represented in the image data, to yield a second determination, obtain a comparison of a position of the imaging device, a position of the anatomical element, and a position of the reference target, generate, based on the first determination, the second determination, and the comparison, a repositioning requirement for the imaging device, the reference target, or both, transmit second instructions for repositioning at least one of the imaging device and the reference target based on the repositioning requirement, compare the image data to one or more known shapes, determine, based on the comparison of the image data to the one or more known shapes, that an object in the image data correlates to a known shape of the anatomical element, and identify the object as the anatomical element in response to determining that the object in the image data correlates to the known shape of the anatomical element.

17. The system of claim 16, wherein the memory further includes instructions that, when executed, cause the processor to:

determine, using the image processing algorithm, that the amount of the anatomical element that is represented in second image data comprises less than all of the anatomical element to yield a third determination, generate, based on the third determination, a second repositioning requirement, and transmit third instructions for repositioning the imaging device based on the second repositioning requirement.

18. The system of claim 17, wherein the third instructions are configured to cause automatic repositioning of the imaging device.

19. The system of claim 16, wherein the anatomical element corresponds to a vertebral anatomy.

20. The system of claim 16, wherein the imaging device is a fluoroscopy device.

* * * * *